(12) United States Patent
Flanagan et al.

(10) Patent No.: US 7,883,736 B2
(45) Date of Patent: Feb. 8, 2011

(54) ENDOPROSTHESES HAVING POROUS CLADDINGS PREPARED USING METAL HYDRIDES

(75) Inventors: Aiden Flanagan, Galway (IE); Barry O'Brien, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 104 days.

(21) Appl. No.: 11/851,127

(22) Filed: Sep. 6, 2007

(65) Prior Publication Data

US 2009/0068339 A1    Mar. 12, 2009

(51) Int. Cl.
*A61L 33/00* (2006.01)
(52) U.S. Cl. .................. 427/2.24; 75/208; 438/250; 427/35; 427/125; 427/229; 427/190; 427/191; 427/194; 427/376.3; 427/376.4; 427/376.5; 427/34; 427/53.1
(58) Field of Classification Search ......... 438/250–253, 438/393, 396, 785, 680; 427/35, 125, 229, 427/190, 191, 194, 376.3, 376.4, 376.5, 34, 427/53.1; 75/208
See application file for complete search history.

(56) References Cited

U.S. PATENT DOCUMENTS

| | | | | |
|---|---|---|---|---|
| 3,345,134 | A | * | 10/1967 | Heymer et al. ............... 423/411 |
| 3,905,777 | A | | 9/1975 | Lacroix |
| 4,374,669 | A | * | 2/1983 | Mac Gregor ................... 419/9 |
| 4,400,408 | A | * | 8/1983 | Asano et al. ................... 419/8 |
| 5,195,969 | A | | 3/1993 | Wang et al. |
| 5,270,086 | A | | 12/1993 | Hamlin |
| 5,366,504 | A | | 11/1994 | Andersen et al. |
| 5,780,807 | A | | 7/1998 | Saunders |
| 6,120,660 | A | | 9/2000 | Chu |
| 6,726,712 | B1 | | 4/2004 | Raeder-Devens et al. |
| 7,294,409 | B2 | | 11/2007 | Lye et al. |
| 7,713,573 | B2 | | 5/2010 | Owens et al. |
| 2004/0167612 | A1 | | 8/2004 | Grignani et al. |
| 2004/0260391 | A1 | | 12/2004 | Santini et al. |
| 2005/0037052 | A1 | | 2/2005 | Udipi et al. |
| 2005/0070989 | A1 | | 3/2005 | Lye et al. |
| 2005/0079201 | A1 | | 4/2005 | Rathenow et al. |
| 2005/0192657 | A1 | | 9/2005 | Colen et al. |
| 2005/0261760 | A1 | | 11/2005 | Weber |
| 2006/0002810 | A1 | | 1/2006 | Grohowski |

(Continued)

FOREIGN PATENT DOCUMENTS

EP     0 875 218     2/2005

(Continued)

OTHER PUBLICATIONS

Man et al., "Laser fabrication of porous surface layer on NiTi shape memory alloy," *Materials Science and Engineering A*, 2005, 404:173-178.

(Continued)

*Primary Examiner*—Michael Barr
*Assistant Examiner*—Andrew Bowman
(74) *Attorney, Agent, or Firm*—Fish & Richardson P.C.

(57) ABSTRACT

A process for making an endoprosthesis comprising: (a) applying a powder that includes a metal hydride to a surface of a metal endoprosthesis, or precursor tubing thereof; and (b) exposing the powder to a heat source to melt the powder and liberate hydrogen gas, thereby forming a porous coating on the surface of the endoprosthesis, or precursor tubing thereof.

31 Claims, 2 Drawing Sheets

U.S. PATENT DOCUMENTS

| | | |
|---|---|---|
| 2006/0121080 A1 | 6/2006 | Lye et al. |
| 2006/0129215 A1 | 6/2006 | Helmus et al. |
| 2006/0141702 A1* | 6/2006 | Woo et al. .................. 438/250 |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0276877 A1 | 12/2006 | Owens et al. |
| 2006/0276878 A1 | 12/2006 | Owens et al. |
| 2006/0276884 A1 | 12/2006 | Lye et al. |
| 2006/0276885 A1 | 12/2006 | Lye et al. |
| 2008/0086198 A1 | 4/2008 | Owens et al. |

FOREIGN PATENT DOCUMENTS

| | | |
|---|---|---|
| RU | 2 218 242 | 12/2003 |
| WO | WO 91/16012 | 10/1991 |
| WO | WO 00/30610 | 6/2000 |
| WO | WO 02/066693 | 8/2002 |

OTHER PUBLICATIONS

Authorized Officer Elena Ovejero, International Search Report/Written Opinion, PCT/US2008/72626 mailed Jul. 1, 2009, 16 pages.

György et al., "Influence of the ambient gas in laser structuring of the titanium surface," *Surface & Coatings Technology*, 2004, 187:245-249.

Authorized Officer Peggy Willis, International Search Report/Written Opinion in PCT/US07/83432 mailed Nov. 2, 2007, 16 pages.

Authorized Officer Agnes Wittmann-Regis, International Preliminary Report on Patentability in PCT/US07/83432 mailed May 14, 2009, 10 pages.

Office Action in U.S. Appl. No. 11/934,415 mailed Jun. 17, 2009, 19 pages.

Fish & Richardson, Amendment in Reply to Office Action of Jun. 17, 2009 in U.S. Appl. No. 11/934,415 mailed Jul. 31, 2009, 9 pages.

Authorized officer Beate Giffo-Schmit, International Preliminary Report on Patentability in PCT/US2008/72626 mailed Mar. 18, 2010, 11 pages.

* cited by examiner

US 7,883,736 B2

ENDOPROSTHESES HAVING POROUS CLADDINGS PREPARED USING METAL HYDRIDES

TECHNICAL FIELD

This invention relates to a process for making endoprostheses, such as stents.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

The endoprosthesis can carry a drug, such as an antiproliferative, to reduce the likelihood of restenosis, i.e., reclosure of the vessel due to immune reactions by the body at the treatment site.

SUMMARY

There is described a process for making an endoprosthesis that includes: (a) applying a powder that includes a metal hydride to a surface of a metal endoprosthesis, or precursor tubing thereof, and (b) exposing the powder to a heat source to melt the powder and liberate hydrogen gas, thereby forming a porous cladding on the surface of the endoprosthesis, or precursor tubing thereof. The heat source could be a laser. The endoprosthesis could be a stent. The porous cladding could include a porous region characterized by a first porosity and a second portion overlying the porous portion characterized by a second porosity that is lower than the first porosity. In some embodiments, the second portion could be substantially non-porous.

A plurality of holes could be provided in the second portion of the porous cladding, and a drug incorporated in the cladding to create a drug eluting endoprosthesis. Alternatively, at least some of the second portion of the porous cladding could be removed to expose the underlying porous portion and thereby provide a surface that could encourage endothelial growth upon implantation in the lumen of a patient. In addition, a drug could be incorporated the exposed underlying porous portion of the cladding, followed by creation of a second, overlying porous cladding or a porous membrane, to create a drug eluting endoprosthesis.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
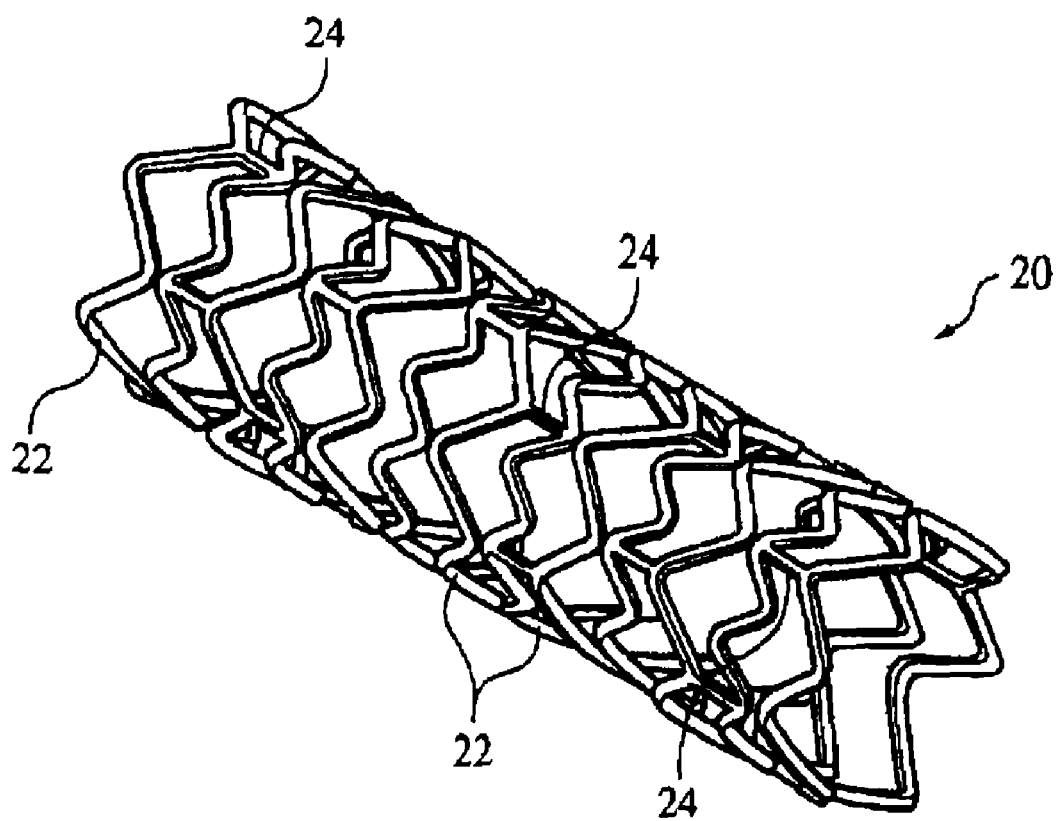
FIG. 1 is a perspective view of an embodiment of an expanded stent.

FIG. 1 depicts an endoprosthesis in the form of a stent 20. Stent 20 could have the form of a tubular member defined by a plurality of bands 22 and a plurality of connectors 24 that extend between and connect adjacent bands. During use, bands 22 could be expanded from an initial, small diameter to a larger diameter to contact stent 20 against a wall of a vessel, thereby maintaining the patency of the vessel. Connectors 24 could provide stent 20 with flexibility and conformability that allow the stent to adapt to the contours of the vessel.

Stent 20 could be of a desired shape and size (e.g., coronary stents, aortic stents, peripheral vascular stents, gastrointestinal stents, urology stents, and neurology stents). Depending on the application, stent 20 could have a diameter of between, for example, 1 mm to 46 mm. In certain embodiments, a coronary stent could have an expanded diameter of from 2 mm to 6 mm. In some embodiments, a peripheral stent could have an expanded diameter of from 5 mm to 24 mm. In certain embodiments, a gastrointestinal and/or urology stent could have an expanded diameter of from 6 mm to about 30 mm. In some embodiments, a neurology stent could have an expanded diameter of from about 1 mm to about 12 mm. An abdominal aortic aneurysm (AAA) stent and a thoracic aortic aneurysm (TAA) stent could have a diameter from about 20 mm to about 46 mm. Stent 20 could be balloon-expandable, self-expandable, or a combination of both (see, e.g., U.S. Pat. No. 5,366,504).

Stent 20 could be delivered to a desired location within a body lumen and expanded using a catheter delivery system. Catheter delivery systems are described in, for example, Wang U.S. Pat. No. 5,195,969, Hamlin U.S. Pat. No. 5,270,086, and Raeder-Devens, U.S. Pat. No. 6,726,712. Stents and stent delivery systems are also exemplified by the Radius® or Symbiot® systems, available from Boston Scientific Scimed, Maple Grove, Minn.

Figure 2:
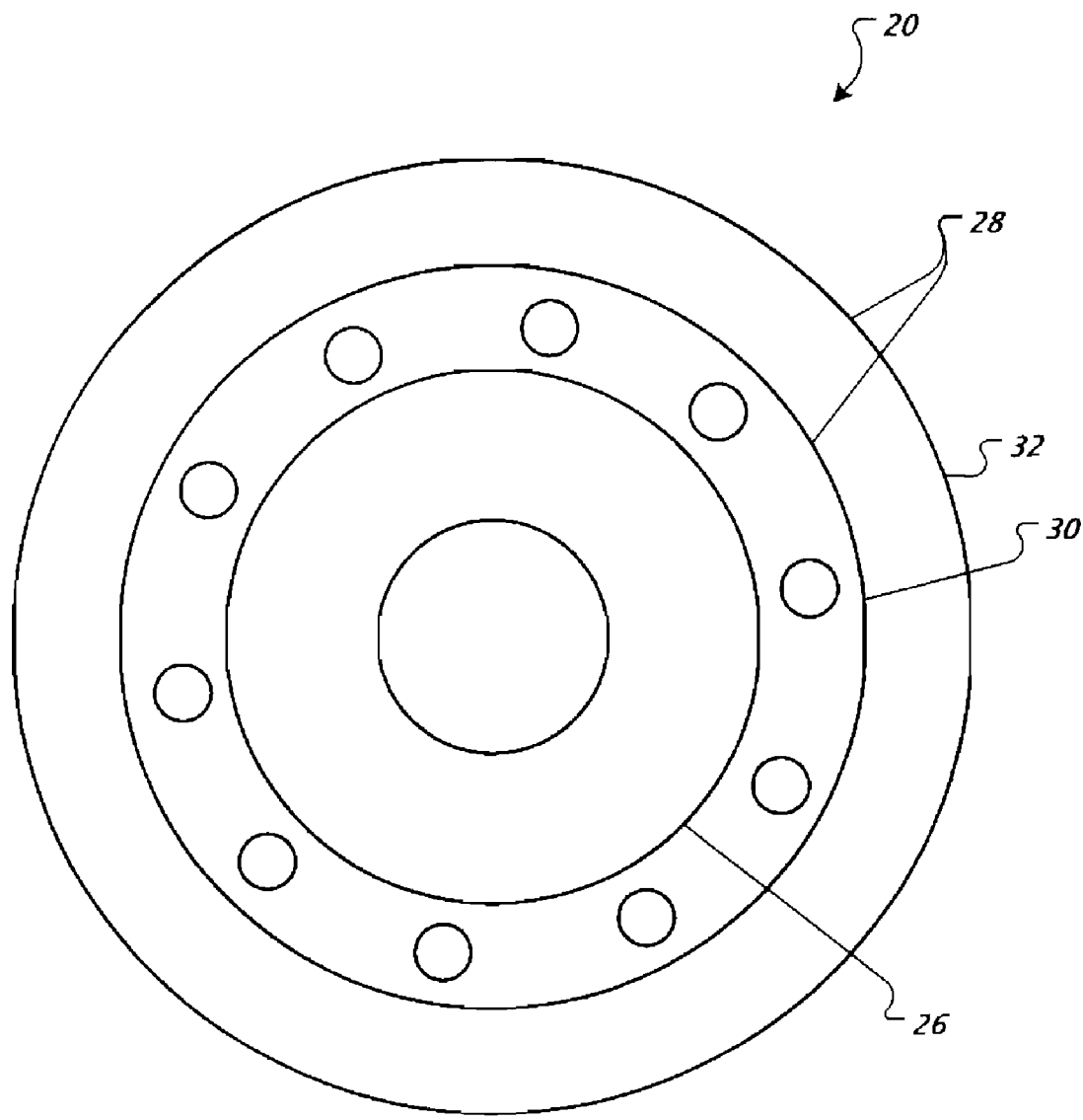
FIG. 2 is a cross-sectional view of a portion of the stent illustrated in FIG. 1.

Referring to FIG. 2, all or a portion of stent 20 could include a base portion 26 provided with a porous cladding 28. In FIG. 2, porous cladding 28 is shown on the outer surface of stent 20. However, it would also be possible to include porous cladding 28 on the inner surface of stent 20.

Porous cladding 28 could include an outer "capping" layer 30 and an underlying porous layer 32. Capping layer 30 could have a porosity that is lower than the porosity of the underlying porous layer 32, and preferably could be substantially non-porous.

Porous cladding 28 could be formed by applying a metal hydride-containing powder to the base portion 26 of stent 20. Examples of suitable materials for base portion 26 could include titanium alloys and composites (e.g., nickel-titanium alloys, commonly referred to as "Nitinol" alloys), niobium alloys and composites, cobalt-chromium alloys, stainless steel, and the like. Examples of suitable metal hydride-containing powders could include transition metal hydrides such as titanium hydride, zirconium hydride, and the like. To promote adhesion between the porous cladding and the base portion, the powder could also include a metal powder in which the metal is the same as one of the metals in the base portion. For example, if the base portion includes a nickel-titanium alloy, the metal hydride-containing powder could contain a mixture of titanium hydride powder and titanium metal powder.

The metal hydride-containing powder could be applied to base portion 26 of stent 20 in the form of a thin coating by coating techniques such as spraying, roll coating, stencil printing, dipping, and the like. Adhesion promoters could be added to the powder to promote initial adhesion between the powder and base portion 26 of stent 20. Following the coating step, the powder coating could be exposed to a heat source to melt the powder and liberate hydrogen gas. As the gas escapes, it creates pores, thereby resulting in the formation of porous cladding 28 on base portion 26.

Suitable heat sources are capable of delivering energy quickly such that the powder is melted, but not the underlying base portion 26 of the stent. Particularly useful heat sources could include lasers. The lasers could be continuous wave lasers or pulsed lasers. Specific examples could include YAG lasers and $CO_2$ lasers. Other examples of potentially useful heat sources include radiofrequency heat sources capable of producing eddy currents.

The laser exposure could take place in an inert atmosphere. Alternatively, it could take place in the presence of a gas such as oxygen or nitrogen. Using an oxygen-containing atmosphere could create metal oxide porous claddings, while a nitrogen-containing atmosphere could create metal nitride porous claddings.

The resulting porous cladding 28 could include an outer capping layer 30 and an underlying porous layer 32. Capping layer 30 could have a porosity that is lower than the porosity of the underlying porous layer 32, and preferably could be substantially non-porous. The particular characteristics of the layers 30 and 32 would depend on both the composition of the metal hydride-containing powder and the heating conditions. For example, increasing the amount of metal hydride in the powder could result in smaller and/or fewer pores, and could favor the formation of closed pores.

Capping layer 30 could be treated with a separate laser to ablate all or selected portions of the layer to create pores in the capping layer. The resulting stent could thus feature a porous cladding having an underlying porous layer and an overlying surface layer with pores that are smaller than the pores of the underlying porous layer. This structure could be useful, e.g., as a drug eluting stent. The underlying porous layer could act as a reservoir for the drug, while the smaller pores of the overlying capping layer could control the elution rate of the drug. Examples of suitable drugs that could be incorporated into the pores are well-known include therapeutic agents such as Paclitaxel. The drugs could be incorporated into the pores using conventional techniques that include exposing the stent to a vacuum, followed by spraying the drug onto the stent to force the drug into the pores, or by exposing the stent to a solution of the drug to imbibe the drug into the pores. Supercritical $CO_2$ could also be used to incorporate a drug into the pores.

Suitable lasers for ablating crust layer 30 could include lasers such as femtosecond lasers and excimer lasers that deliver very rapid bursts of energy. The size, number, and condition of the holes (e.g., open-cell vs. closed-cell) could be selected by selecting appropriate laser exposure conditions.

It also would be possible to remove all or a selected portion of capping layer 30 completely using the laser. This would expose the underlying porous layer 32, thereby creating a surface that could promote endothelialization (i.e., a "pro-healing" surface).

In another embodiment, all or a selected portion of capping layer 30 could be removed to expose the underlying porous layer 32. Drug could then be incorporated into the pores of porous layer 32. The resulting structure could then be provided with an overlying porous membrane (e.g., a polymeric or inorganic membrane) to form a drug eluting stent. Alternatively, a second porous cladding, having a second porous layer and a second capping layer, could be created on top of porous layer 32 following the above-described process. The second porous cladding could then be treated (e.g., by ablating all or a portion of the second capping layer to create pores or to remove the second capping layer) to create a drug eluting stent. In these embodiments, the pore size of the structure could be fine-tuned to control the drug eluting properties of the stent.

In yet another embodiment for creating a drug eluting stent, the drug could be deposited directly on the endoprosthesis surface, followed by creation of the cladding layer 28 and subsequent ablation of the capping layer 30.

Porous cladding 28 could be created on the stent itself, after the stent has been formed from precursor tubing. Alternatively, porous cladding 28 could be created on the precursor tubing, which could be processed subsequently to form the stent.

EXAMPLES

Example 1

A stent made of Stainless Steel 316LVM is provided. A powder mixture is coated onto the surface of the stent by spraying, roll coating, stencil printing, dipping, or the like to form a thin coating on the surface of the stent. The powder mixture contains an adhesive or fluid additive, and is in the form of a paste to promote adhesion to the stent surface. The powder mixture also contains particles of titanium hydride and SS316 stainless steel in portions chosen to achieve a predetermine porosity in the final coating. The paste is left to dry on the surface of the stent. A laser is then used to melt the paste in a nitrogen atmosphere. The molten material cools and forms a porous cladding on the surface of the stent as hydrogen outgases. The nitrogen in the surrounding atmosphere combines with some of the titanium in the molten powder to form titanium nitride (TiN). The final porous cladding contains an outer skin overlying a porous network. Another laser is then used to bore multiple holes having diameters less about 1 micron in the outer skin to enable access to the porous network. A solution of drug is then introduced into the porous network via the holes to form a drug eluting stent.

Example 2

A tube made of Stainless Steel 316LVM is provided. A powder mixture is coated onto the surface of the tube by spraying, roll coating, stencil printing, dipping, or the like to form a thin coating on the surface of the tube. The powder mixture contains an adhesive or fluid additive, and is in the form of a paste to promote adhesion to the tube surface. The powder mixture also contains particles of titanium hydride and SS316 stainless steel in portions chosen to achieve a predetermine porosity in the final coating. The paste is left to dry on the surface of the tube. A laser is then used to melt the paste. The molten material cools and forms a porous cladding on the surface of the tube as hydrogen outgases. The tube is later cut into a stent using the same or different laser to expose sides of the porous coating, thereby creating a stent with an abluminal porous coating that can be used for abluminal drug delivery.

Example 3

A stent made of Nitinol (NiTi) is provided. A powder mixture is coated onto the surface of the stent by spraying, roll coating, stencil printing, dipping, or the like to form a thin coating on the surface of the stent. The powder mixture contains an adhesive or fluid additive, and is in the form of a paste to promote adhesion to the stent surface. The powder mixture also contains particles of titanium hydride and NiTi in portions chosen to achieve a predetermine porosity in the final coating. The paste is left to dry on the surface of the stent. A laser is then used to melt the paste in a nitrogen atmosphere. The molten material cools and forms a porous cladding on the surface of the stent as hydrogen outgases. The nitrogen in the surrounding atmosphere combines with some of the titanium in the molten powder to form titanium nitride (TiN). The final porous cladding contains an outer skin overlying a porous network. Another laser is then used to bore multiple holes having diameters less about 1 micron in the outer skin to enable access to the porous network. A solution of drug is then introduced into the porous network via the holes to form a drug eluting stent. The inside surface of the stent is ablated using a laser to expose the underlying porous network and form a surface that promotes endothelial cell growth.

Example 4

A stent made of Nitinol (NiTi) is provided. A powder mixture is coated onto the surface of the stent by spraying, roll coating, stencil printing, dipping, or the like to form a thin coating on the surface of the stent. The powder mixture contains an adhesive or fluid additive, and is in the form of a paste to promote adhesion to the stent surface. The powder mixture also contains particles of titanium hydride and NiTi in portions chosen to achieve a predetermine porosity in the final coating. The paste is left to dry on the surface of the stent. A laser is then used to melt the paste in an oxygen atmosphere. The molten material cools and forms a porous cladding on the surface of the stent as hydrogen outgases. The oxygen in the surrounding atmosphere combines with some of the titanium in the molten powder to form titanium oxide. The final porous cladding contains an outer skin overlying a porous network. Another laser is then used to bore multiple holes having diameters less about 1 micron in the outer skin to enable access to the porous network. A solution of drug is then introduced into the porous network via the holes to form a drug eluting stent. The inside surface of the stent is ablated using a laser to expose the underlying porous network and form a surface that promotes endothelial cell growth.

Example 5

A stent made of a titanium alloy is provided for use as an MRI compatible stent. A powder mixture is coated onto the surface of the stent by spraying, roll coating, stencil printing, dipping, or the like to form a thin coating on the surface of the stent. The powder mixture contains an adhesive or fluid additive, and is in the form of a paste to promote adhesion to the stent surface. The powder mixture also contains particles of titanium hydride and titanium in portions chosen to achieve a predetermine porosity in the final coating. The paste is left to dry on the surface of the stent. A laser is then used to melt the paste in a nitrogen atmosphere. The molten material cools and forms a porous cladding on the surface of the stent as hydrogen outgases. The nitrogen in the surrounding atmosphere combines with some of the titanium in the molten powder to form titanium nitride (TiN). The final porous cladding contains an outer skin overlying a porous network. Another laser is then used to bore multiple holes having diameters less about 1 micron in the outer skin to enable access to the porous network. A solution of drug is then introduced into the porous network via the holes to form a drug eluting stent.

Example 6

A stent made of a titanium alloy is provided for use as an MRI compatible stent. A powder mixture is coated onto the surface of the stent by spraying, roll coating, stencil printing, dipping, or the like to form a thin coating on the surface of the stent. The powder mixture contains an adhesive or fluid additive, and is in the form of a paste to promote adhesion to the stent surface. The powder mixture also contains particles of zirconium hydride and titanium in portions chosen to achieve a predetermine porosity in the final coating. The paste is left to dry on the surface of the stent. A laser is then used to melt the paste in a nitrogen atmosphere. The molten material cools and forms a porous cladding on the surface of the stent as hydrogen outgases. The nitrogen in the surrounding atmosphere combines with some of the zirconium and titanium in the molten powder to form titanium nitride (TiN) and zirconium nitride (ZrN). The final porous cladding contains an outer skin overlying a porous network.

A number of embodiments have been described. Nevertheless, it will be understood that various modifications may be made without departing from the spirit and scope of the invention. Accordingly, other embodiments are within the scope of the following claims.

What is claimed is:

1. A process for making an endoprosthesis comprising:
   (a) applying a powder comprising a metal hydride to a surface of a metal endoprosthesis, or precursor tubing thereof; and
   (b) exposing the powder to a heat source to melt the powder and liberate hydrogen gas, thereby forming a porous cladding on the surface of the endoprosthesis, or precursor tubing thereof, the porous cladding having a first porosity; and
   (c) forming a capping layer over the porous cladding, the capping layer having a second porosity that is lower than the first porosity.

2. A process according to claim 1 wherein the heat source comprises a laser.

3. A process according to claim 2 wherein the laser is selected from the group consisting of continuous wave lasers and pulsed lasers.

4. A process according to claim 2 wherein the laser comprises a YAG laser.

5. A process according to claim 2 wherein the laser comprises a CO2 laser.

6. A process according to claim 1 wherein the endoprosthesis comprises a titanium alloy or composite.

7. A process according to claim 6 wherein the endoprosthesis comprises a nickel-titanium alloy.

8. A process according to claim 6 wherein the endoprosthesis comprises stainless steel.

9. A process according to claim 1 wherein the powder comprises titanium hydride powder.

10. A process according to claim 1 wherein the powder comprises zirconium hydride powder.

11. A process according to claim 1 wherein the powder further comprises a metal powder.

12. A process according to claim 11 wherein the metal powder comprises titanium metal powder.

13. A process according to claim 1 comprising exposing the powder to the heat source in the presence of oxygen to create a porous coating comprising a metal oxide.

14. A process according to claim 1 comprising exposing the powder to the heat source in the presence of nitrogen to create a porous cladding comprising a metal nitride.

15. A process according to claim 1 wherein the capping layer is substantially non-porous.

16. A process according to claim 1 further comprising creating a plurality of holes in the capping layer.

17. A process according to claim 16 comprising using a laser to create the plurality of holes.

18. A process according to claim 16 further comprising incorporating a drug into the porous cladding to create a drug eluting endoprosthesis.

19. A process according to claim 1 further comprising removing at least some of the capping layer to expose the underlying porous portion of the cladding.

20. A process according to claim 19 further comprising incorporating a drug into the exposed underlying porous portion of the cladding.

21. A process according to claim 20 further comprising:
(a) applying a powder comprising a metal hydride to the exposed porous portion of the cladding; and
(b) exposing the powder to a heat source to melt the powder and liberate hydrogen gas, thereby forming a second porous cladding on the exposed porous portion.

22. A process according to claim 1 wherein the endoprosthesis comprises a stent.

23. A process according to claim 1 wherein the endoprosthesis, or precursor tubing thereof, comprises an inner surface and an outer surface, the process comprising applying the powder to the inner surface.

24. A process according to claim 1 wherein the endoprosthesis, or precursor tubing thereof, comprises an inner surface and an outer surface, the process comprising applying the powder to the outer surface.

25. A process according to claim 1 comprising depositing a drug on the surface of the endoprosthesis, or precursor tubing thereof, prior to applying the powder.

26. A process for making a stent comprising:
(a) applying a powder comprising a metal hydride to a surface of a metal stent, or precursor tubing thereof, selected from the group consisting of nickel-titanium alloy stents, stainless steel stents, and combinations thereof; and
(b) exposing the powder to a laser to melt the powder and liberate hydrogen gas, thereby forming a porous cladding on the surface of the stent, or precursor tubing thereof,
wherein the porous cladding comprises a porous region characterized by a first porosity and a capping layer overlying the porous portion characterized by a second porosity that is lower than the first porosity.

27. A process according to claim 26 wherein the capping layer is substantially non-porous.

28. A process according to claim 26 further comprising creating a plurality of holes in the capping layer.

29. A process according to claim 28 comprising using a laser to create the plurality of holes.

30. A process according to claim 28 further comprising incorporating a drug into the porous cladding to create a drug eluting stent.

31. A process according to claim 26 further comprising removing at least some of the capping layer to expose the underlying porous portion of the porous cladding.

* * * * *